(12) United States Patent
Wells et al.

(10) Patent No.: US 6,543,273 B1
(45) Date of Patent: Apr. 8, 2003

(54) EFFICIENT USE OF METALLIC MATERIALS FOR DYNAMIC TEAR TESTING

(75) Inventors: Michael E. Wells, New Carrollton, MD (US); Robert DeNale, Ijamsville, MD (US); Roy A. Lindauer, Ridgley, MD (US); Ralph W. Judy, Jr., Annandale, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 268 days.

(21) Appl. No.: 09/637,108

(22) Filed: Aug. 11, 2000

Related U.S. Application Data

(60) Provisional application No. 60/152,137, filed on Aug. 17, 1999.

(51) Int. Cl.[7] .............................. G01M 7/00; G01N 3/08
(52) U.S. Cl. ...................................... 73/12.01; 73/835
(58) Field of Search ............................ 73/12.01, 12.04, 73/12.06, 835

(56) References Cited

U.S. PATENT DOCUMENTS 3,583,215 A * 6/1971 Franz ........................ 73/12.01
5,092,179 A * 3/1992 Ferguson .................... 73/790
5,450,742 A * 9/1995 Baltz et al. ................ 73/12.06

* cited by examiner

Primary Examiner—Max Noori
(74) Attorney, Agent, or Firm—Howard Kaiser

(57) ABSTRACT

A unitary test piece which dimensionally conforms with standardized dynamic tear testing guidelines comprises a middle section and two end sections welded thereto. The middle section is made of the test-subject metallic material. The two end sections are each made of a metallic material which is compatible with the test-subject metallic material, and primarily serve the purpose of combining with the middle section at its longitudinal ends in order to together form the dimensionally suitable test piece. The length of the middle section is at least the minimum such length that will totally encompass plastic deformation of such metallic material when subjected to dynamic tear testing, this depending on the nature of such metallic material. Ferrous end sections are compatible with a ferrous middle section; non-ferrous end sections of a particular designation are compatible with a non-ferrous middle section of the same designation. The invention advantageously permits economical utilization of test-subject metallic material under circumstances in which available samples thereof are expensive, limited, inappropriately or problematically sized, inappropriately or problematically configured, and/or intended to be tested for one or more properties in addition to dynamic tear.

24 Claims, 13 Drawing Sheets

| Material | Thickness inch | Width inch | Length inch |
|---|---|---|---|
| Ti-6Al- 4V | 1.00 ± 0.06 | 4.75 ± 0.12 | 18.0 ± 0.12 |

| Material | Section | Thickness inch | Width inch | Length inch |
|---|---|---|---|---|
| Ti-6Al-4V | Center | 1.00 ± 0.06 | 4.75 ± 0.12 | 5.0 ± 0.020 |
| Ti-6Al-4V | End-tabs | 1.00 ± 0.06 | 4.75 ± 0.12 | 6.5 ± 0.050 |

| Weld | Kilovolts kV | Milli-amps mA | Focus | Deflection | | | Travel Speed IPM | Work Distance inch |
|---|---|---|---|---|---|---|---|---|
| | | | | Beam Pattern # | Frequency Hz | Size inch | | |
| Seal | 150 | 15 | Sharp | 5 (circle) | 800 | 0.025 | 30 | 10.5 |
| Pass | 150 | 15 | Sharp | 5 (circle) | 800 | 0.025 | 15 | 10.5 |
| Cosmetic | 150 | 15 | Sharp | 5 (circle) | 800 | 0.025 | 15 | 10.5 |

| Parameter | Dimension, inch |
|---|---|
| Test material, $T_m$ | 3.0 ±0.04 |
| Notch width | 0.062 |
| Notch depth | 0.062 |
| Notch length | 1.75 nominal |

| Weld | Kilovolts kV | Milli-amps mA | Focus | Deflection | | | Speed IPM | Work Distance in |
|---|---|---|---|---|---|---|---|---|
| | | | | Beam Pattern | Frequency Hz | Size in | | |
| Seal | 100 | 3 | Sharp | 8 (arrow) | 800 | 0.04 | 30 | 11.0 |
| Pass | 100 | 40 | Sharp | 8 (arrow) | 800 | 0.40 | 15 | 10.5 |

FIG. 5

| Specimen Type | Specimen ID | Tear Energy ft-lbs | Fracture mode |
|---|---|---|---|
| Nonstandard | 1 | 687 | Mixed mode |
| | 2 | 793 | Mixed mode |
| | 3 | 890 | Mixed mode |
| | 4 | 793 | Mixed mode |
| | Average | 790 | |
| | | | |
| Standard | 5 | 746 | Mixed mode |
| | 6 | 805 | Mixed mode |
| | 7 | 770 | Mixed mode |
| | 8 | 841 | Mixed mode |
| | Average | 790 | |
| | | | |
| | Range* | 331-942 | |
| * Range in impact energy for commercial grade Ti-6Al-4V using the 1-inch DT specimen. | | | |

FIG. 8

Length of Center Test Section

| Titanium Alloy | Length, in |
|---|---|
| Unalloyed grades | 5 |
| Alpha and near alpha alloys | 4 |
| Alpha-beta alloys | 3 |
| Beta alloys | 2 |

FIG. 6A  FIG. 6B

| Parameter | Dimension, inch |
|---|---|
| Test material, $T_m$ | 3.0 ± 0.04 |
| Tension Edge Notch Thickness | 0.062 |
| Tension Edge Notch Depth | 0.25 |

| Parameter | Dimension, inch |
|---|---|
| Vertical drop height | 8.872 feet |
| Hammer weight | 1721.3 pounds |
| Tup radius | 1.0-inch |
| Anvil radius | 5/8-inch |
| Support span, S | 16-inches |

EFFICIENT USE OF METALLIC MATERIALS FOR DYNAMIC TEAR TESTING

This application claims the benefit of U.S. Provisional Application No. 60/152,137, filed Aug. 17, 1999, entitled "Dynamic Tear Testing of Metallic Materials," incorporated herein by reference.

The invention described herein may be manufactured and used by or for the Government of the United States of America for governmental purposes without the payment of any royalties thereon or therefor.

BACKGROUND OF THE INVENTION

The present invention relates to methods and apparatuses for testing properties of materials, more particularly to methods and apparatuses for testing impact fracture toughness (resistance) of metallic materials such as titanium.

The "dynamic tear" (DT) test is a conventional procedure for characterizing impact fracture toughness properties of both ferrous and nonferrous materials. The "one-inch standard" DT test was developed at the United States Naval Research Laboratory (NRL) in the early 1960's.

Since the mid-1960's, the one-inch DT test has been used extensively by the U.S. Navy to characterize the impact fracture resistance of high strength steels, titanium alloys and aluminum alloys. Numerous U.S. Navy specifications require the use of the standard specimen for measuring the impact fracture toughness of candidate marine construction materials. DT test facilities have been established by the U.S. Navy at various research laboratories and production plants in this country and abroad.

Incorporated herein by reference, and appended hereto marked "APPENDIX A," is the following U.S. Navy report (NRL FR-6851) which describes the standard specimen and procedure in accordance with the one-inch DT test: Puzak, P. P. and F. A. Lange, "Standard Method for the 1-inch Dynamic Tear Test," NRL Report 6851, February 1969. Essentially, as described by Puzak et al. in APPENDIX A, the standard one-inch DT test involves the impacting of a large beam which contains a brittle crack starter weld on the tension side of the standard specimen. The dimensions of the standard specimen are 1 inch thick×4.75 inches wide×18 inches long.

Also incorporated herein by reference are the following U.S. Navy reports: NRL FR-7159, E. A. Lange, P. P. Puzak and L. A. Cooley, "Standard Method for the ⅝ Inch Dynamic Tear Test," 1970; NRL FR-6975, E. A. Lange and F. J. Loss, "Dynamic Tear Energy—A Practical Performance Criterion for Fracture Resistance," 1969; NRL FR-6991, C. N. Freed and R. J. Goode, "Relationship between Fracture Toughness and Estimated Plastic Zone Size in Steel, Titanium and Aluminum Alloys," 1969; NRL FR-6873, R. W. Judy, P. P. Puzak and E. A. Lange, "Characterization of Fracture Toughness of 5Ni—Cr—Mo—V Steel by Charpy V-Notch and Dynamic Tear Tests," 1969; NRL FR-6864, G. E. Nash, "An Analysis of the Forces and Bending Moments Generated during the Dynamic Tear Test," 1969; R-1969-14151, G. E. Nash, E. A. Lange, "Mechanical Aspects of the Dynamic Tear Test," 1969; NRL MR-1826, G. E. Nash and E. A. Lange, "Mechanical Aspects of the Dynamic Tear Test Specimen," 1967; R-1970-14063, E. A. Lange and F. J. Loss, "Dynamic Tear Energy—A Practical Peformance Criterion for Fracture Resistance," 1970; NRL FR-7056, F. J. Loss, "Dynamic Tear Test Investigations of the Fracture Toughness of Thick-Section Steel," 1970; NRL FR-6993, L. A. Cooley and E. A. Lange, "Vertical Drop-Weight Machine for Conducting Drop-Weight NDT, Drop-Weight Tear and Dynamic Tear Tests," 1970; R-1977-14178, T. G. Heberling, E. S. Harris and E. A. Lange, "Results of Interlaboratory Test Programs to Evaluate the ⅝-in. (16-mm) Dynamic Tear Test Method," 1977.

According to the one-inch standard DT test, the brittle crack starter weld is prepared by machining a shallow 1.75 inch long groove across the width on each of both sides of the specimen. A small amount of embrittling material is diffused in an electron beam weld through the 1-inch plate thickness. For a titanium specimen, steel wires are placed in the grooves and upset by light hammering to ensure uniform distribution of the embrittling materials during electron beam (EB) welding. After EB welding the crack starter weld is notched to assist initiation of the crack in the embrittled weld. The specimen is fractured using a pendulum machine (or drop-weight machine), and the total energy for fracture is recorded.

The main disadvantage associated with use of the standard one-inch DT test (to characterize the fracture toughness of materials) is the requisite large size of the test specimen. Although usually one-inch DT testing of flat plate material is readily accomplished, one-inch DT testing of many different product and pre-product forms, such as used in submarine and surface ship construction, are problematical or impractical.

For instance, forgings and castings are frequently of a shape that does not allow the removal of an 18-inch long flat specimen. This necessitates the design and fabrication of special forging dies that produce a sufficient amount of excess material to allow the removal of a DT specimen blank for testing. Another example of the limitedness of the one-inch DT test is its inability to test small mock-up or pre-production forgings, which typically are on the order of 9–12 inches in diameter. The cost of fabricating special forging dies for mock-up or pre-production testing can be prohibitively expensive.

SUMMARY OF THE INVENTION

In view of the foregoing, it is an object of the present invention to provide method and apparatus for testing dynamic tear of a metallic material when there is an insufficient and/or unsuitably dimensioned amount of available metallic material for properly performing the one-inch standard DT test.

It is further object of the present invention to provide method and apparatus for testing dynamic tear of a limited amount of metallic material so that one or more other tests of the metallic material can be properly performed.

The present invention provides a methodology for measuring the dynamic tear toughness properties of metallic materials (such as titanium, steel and aluminum alloys), particularly in cases of limited material availability or incompatible size and geometry. The inventive DT test procedure features utilization of a modified ("nonstandard") DT specimen in lieu of the "standard" one-inch DT specimen. Inventively implemented is a smaller, "nonstandard" DT specimen which will generate energy values equivalent to those which would be measured for the larger, "standard" one-inch DT specimen.

According to this invention, the nonstandard one-inch dynamic tear specimen comprises a center (middle) test section and a pair of end-tabs. The center test section is made of the test material, and is joined (preferably, welded) to each of the two end-tabs. The two end-tabs, when appropriately combined with the center test section, accomplish complete dimensional standardization of the nonstandard one-inch DT specimen.

In other words, according to this invention, the center test section and the two end-tabs each have the standard width and standard thickness, but a "non-standard" length which is something less than the standard length. In typical inventive practice, the two end-tabs will each have the same "non-standard" length, which will exceed the "non-standard" length of the center test section. Once the center test section and two end-tabs are united in the lengthwise direction, the integral whole has become characterized by the standard length as well as the standard width and standard thickness.

In accordance with the present invention, a method is provided for obtaining a rectangular parallelepiped section from an object for the purpose of being subjected to dynamic tear testing of the kind wherein a rectangular parallelepiped specimen made of a metallic material is impacted, wherein the specimen has a prescribed length, a prescribed width and a prescribed thickness, and wherein the specimen has provided therein a crack through the thickness and a portion of the width for initiating fracture of the specimen when impacted. The method comprises: determining the extent of lengthwise plastic deformation of the specimen which would result if the specimen were subjected to the dynamic tear testing; and, obtaining from the object the rectangular parallelepiped section having the prescribed width, the prescribed thickness and a nonprescribed length which is shorter than the prescribed length, the nonprescribed length being at least as great as the determined extent of lengthwise plastic deformation.

Further provided in accordance with the present invention is a method for making a rectangular parallepiped integral entity to be used for the purpose of performing, in relation to an object, dynamic tear testing of the kind wherein a rectangular parallepiped specimen made of a metallic material is impacted, the specimen having a prescribed length, a prescribed width and a prescribed thickness, the specimen having provided therein a crack through the thickness and along a portion of the width for initiating fracture of the specimen when impacted. The method comprises: determining the extent of lengthwise plastic deformation of the specimen which would result if the specimen were subjected to the dynamic tear testing; obtaining from the object a rectangular parallelepiped section having the prescribed width, the prescribed thickness and a section length which is shorter than the prescribed length, the section length being at least as great as the determined extent of lengthwise plastic deformation; and, joining at lengthwise opposite ends of the section a pair of congruent rectangular parallelepiped end-tabs, each end-tab having the prescribed width, the prescribed thickness and an end-tab length which is equal to one-half the difference between the prescribed length and the section length, thereby forming the integral entity having the prescribed length, the prescribed width and the prescribed thickness, the integral entity being adaptable to being used as the specimen for the purpose of performing the dynamic tear testing.

Still further provided by the present invention is a method for performing, in relation to an object, dynamic tear testing of the kind wherein a rectangular parallepiped specimen made of a metallic material is impacted, the specimen having a prescribed length, a prescribed width and a prescribed thickness, the specimen having provided therein a crack through the thickness and along a portion of the width for initiating fracture of the specimen when an impact is caused with respect thereto. The method comprises: determining the extent of lengthwise plastic deformation of the specimen which would result if the specimen were subjected to the dynamic tear testing; obtaining from the object a rectangular parallelepiped section having the prescribed width, the prescribed thickness and a section length which is shorter than the prescribed length, the section length being at least as great as the determined extent of lengthwise plastic deformation; joining at lengthwise opposite ends of the section a pair of congruent rectangular parallelepiped end-tabs, each end-tab having the prescribed width, the prescribed thickness and an end-tab length which is equal to one-half the difference between the prescribed length and the section length, thereby forming the integral entity having the prescribed length, the prescribed width and the prescribed thickness, the integral entity being adaptable to being used as the specimen for performing the dynamic tear testing; providing the crack in said integral entity; and, causing the impact with respect to the integral entity.

In inventive practice, it is not necessary for either end-tab that the material composition of the end-tab match the material composition of the center test section. In fact, it is not even inventively necessary that the end-tabs match each other in terms of material composition. It is inventively necessary, however, that each end-tab have such material composition as to be capable of being welded to the center test section.

As for "weldability" of the end-tabs with respect to the center test section, the end-tabs should be made of a compatible material for such purposes. Metallic materials are broadly classified as either ferrous or non-ferrous. The inventive practitioner should use ferrous end tabs with a ferrous center test section, and should use non-ferrous end tabs with a non-ferrous center test section. Beyond that, inventive practice will generally require that each end tab's material composition belong to the same metallic material grouping as does the center test section's material composition. The U.S. Navy and some other entities use a classification system which provides for five groups or categories of metallic materials, viz., (i) steel, (ii) aluminum and aluminum alloys, (iii) copper and copper alloys, (iv) titanium and titanium alloys, and (v) nickel and nickel alloys. Of these five metallic material categories, steel is ferrous; aluminum/aluminum alloys, copper/copper alloys, titanium/titanium alloys and nickel/nickel alloys are non-ferrous.

In inventive practice, it is generally requisite that the center test section and the two end-tabs all be made of a material which belongs to the same metallic material category. More specifically, a steel center test section should be used with two steel end-tabs. An aluminum or aluminum alloy center test section should be used with two aluminum or aluminum alloy end-tabs. A copper or copper alloy center test section should be used with two copper or copper alloy end-tabs. A titanium or titanium alloy center test section should be used with two titanium or titanium alloy end-tabs. A nickel or nickel alloy center test section should be used with two nickel or nickel end-tabs. Violation of this inventive "same-group" principle will likely compromise the inventive testing.

For instance, titanium is highly reactive with practically all materials. Titanium alloy material reacts with virtually any non-titanium alloy material to form brittle inter-metallic compounds (e.g., in the weld). If, for example, a titanium alloy center test section were used with steel end-tabs, the welds joining the center test section to the end-tabs would be embrittled and hence would compromise the performance of the inventive nonstandard specimen.

According to the present invention, the center section could be made of a first material (e.g., a first titanium alloy), and the end-tabs could each be made of a second material (e.g., a second titanium alloy). Alternatively, the center section could be made of a first material (e.g., a first titanium alloy), one end-tab could be made of a second material (e.g., a second titanium alloy), and the other end-tab could be made of a third material (e.g., a third titanium alloy). Again alternatively, the center section and one end-tab could each be made of a first material (e.g., a first titanium alloy), and the other end-tab could be made of a second material (e.g., a second titanium alloy). Further alternatively, the center section and the end-tabs could each be made of a first material (e.g., a first titanium alloy); that is to say, the center section and end-tabs could all be made of the same material (e.g., the same titanium alloy). An inventive advantage of using at least one end-tab having a different material composition from that of the center section, albeit within the same material grouping, is that such different material composition is readily available at significantly less cost.

The end-tabs are joined to the center test section by means of electron beam welding. The inventive procedures pertaining to (i) electron beam welding of the crack starter, and (ii) notching of the crack starter, are similar to the corresponding procedures used for the standard one-inch dynamic tear specimen.

According to many inventive embodiments involving one-inch dynamic tear testing, the center test section is about five inches wide, and each end-tab is about 6½ inches long. Hence, the test material of the inventive nonstandard DT specimen is approximately 5 inches in length, compared with approximately 18 lengthwise inches of test material on the standard 1-inch DT specimen.

The five inch length of the center test section (for one-inch DT testing) does not represent an arbitrary selection by the inventors; rather, the inventors determined that all of the plastic deformation for the titanium alloys tested was contained within this center section. In generally preferred inventive practice pertaining to one-inch DT testing, the center test section is at least approximately 5 inches long, and (depending on the inventive embodiment) can be shorter than 5 inches.

Five inches is the longest possible center test section length which is reasonably expected to encompass the entirety of plastic deformation, when subjected to one-inch DT testing. Just five inches is an expeditious center test section length for many inventive embodiments involving one-inch DT testing, since the requisite amount of test material is minimized while being fully inclusive of plastic deformation.

The inventive practitioner will be capable of determining the extent of plastic deformation of a particular type of metallic material. This determination will govern the length of the inventive center test section in the dynamic tear testing. This determination is easily accomplished by undertaking "before" and "after" measurements (e.g., using a micrometer) of a standard 18-inch long DT test specimen. First, the width and thickness of the specimen are measured. Then the specimen is subjected to standard 1-inch dynamic tear testing. Then, the specimen is measured again. The practitioner measures the change in thickness from the fracture edge outward (i.e., change in thickness while moving bidirectionally away from the fracture edge). The thickness along the fracture plane (face) is measured by commencing at the center of the specimen and proceeding in opposite directions. The starting point is the center of the specimen. For instance, if the width of the specimen is 4¾ inches, the practitioner commences measurement at 2⅜ inches and proceeds in either direction. The plastic deformation has ceased where the post-test thickness is equal to the pre-test thickness.

U.S. Navy researchers have demonstrated the feasibility of inventive practice using a nonstandard specimen made of the near alpha titanium alloy Ti 6Al—2Cb—1Ta—1Mo and of the alpha-beta titanium alloy Ti 6Al—4V. Incorporated herein by reference, and appended hereto marked "APPENDIX B," is the following U.S. Navy report: Wells, Michael E. and Roy A. Lindauer, "A Test Method for Dynamic Tear Testing of Titanium Plate Using a Nonstandard Specimen," CARDIVNSWC-TR-61-97/11, August 1998, Technical Report, Survivability, Structures and Materials Directorate, Carderock Division, Naval Surface Warfare Center, West Bethesda, Md. 20817-5700.

APPENDIX B discloses how U.S. Navy researches inventively characterized the fracture toughness properties of an alpha-beta titanium alloy. The present invention is described therein in terms of the dimensions and preparation of the specimen, the apparatus and the testing procedure. As disclosed by Wells et al. in APPENDIX B, the inventive nonstandard specimen proved adequate for measuring the fracture energy of titanium alloy Ti 6Al—4V plate. The results of the inventive dynamic tear tests demonstrated that the inventive nonstandard specimen accurately measures the fracture energy of titanium alloy plate.

It is believed, however, that the present invention can be applied to all high strength titanium, steel and aluminum alloys, and to some other metallic materials. Especially in cases of limited or incompatible material availability, the inventive methodology is recommended for characterization of the fracture toughness properties not only of alpha-beta titanium alloys, but of a variety of other metallic materials as well.

As noted hereinabove, titanium alloys Ti 6211 and Ti 6Al—4V were used by the U.S. Navy to demonstrate that the inventive nonstandard DT specimen could be used in lieu of the standard one-inch DT specimen to accurately measure the fracture toughness of near alpha (Ti 6211) and alpha-beta (Ti 6-4) alloys. Nevertheless, since the amount of plastic deformation decreases with increasing strength, the inventors believe it manifest that the nonstandard specimen can be used to test all higher strength titanium alloys.

A preliminary examination of the plastic zone in low strength, commercially pure titanium nonstandard specimens revealed that the plastic deformation did not appear to extend beyond five inches. Therefore, in inventive practice, the maximum length of the center test section is five inches, which will encompass the plastic deformation in all titanium alloys. It is believed likely that this specimen's dimensional configuration can also be applied to all titanium alloys and to steel and aluminum alloys (and other metallic materials) of comparable strength.

In accordance with the present invention, the center test section should have a length which ensures complete envelopment of the plastic deformation which it shall experience upon undergoing dynamic tear testing. As a general "rule of thumb" for inventive practice involving one-inch dynamic tear testing, five inches is the maximum length which, regardless of the material of the center test section, will guarantee inclusion of its plastic deformation when it is subjected to the one-inch dynamic tear testing. However, some metallic materials lend themselves to inventive dynamic tear testing using a center test section which is less, perhaps much less, than five inches long.

In this regard, specific inventive guidelines for selecting center test section length can be inventively ascertained for different types of materials in accordance with subcategorizations thereof. It is recalled that five categories of metallic materials are conventionally recognized, viz., (i) steel, (ii) aluminum and aluminum alloys, (iii) copper and copper alloys, (iv) titanium and titanium alloys, and (v) nickel and nickel alloys. For instance, the "titanium and titanium alloy" metallic material category is conventionally grouped into four groups, designations or subcategories, viz., (i) the unalloyed or commercially pure subcategory, (ii) the alpha and near alpha subcategory, (iii) the alpha-beta subcategory, and (iv) the beta subcategory. It has been inventively determined that, in relation to one-inch DT testing, the minimum center test section lengths corresponding to these four subcategories of the titanium/titanium alloy category are as follows: (i) five inches for the unalloyed or commercially pure subcategory, (ii) four inches for the alpha and near alpha subcategory, (iii) three inches for the alpha-beta subcategory, and (iv) two inches for the beta subcategory.

The minimum center test section lengths corresponding to any or all of the four subcategories of the titanium/titanium alloy category can similarly be inventively determined in relation to other-dimensioned (e.g., ⅝ inch) dynamic tear testing. Moreover, the minimum center test section lengths corresponding to any or all of the designations or subcategories of any or all of the remaining metallic material categories (namely, steel, aluminum/aluminum alloys, copper/copper alloys and nickel/nickel alloys), and in relation to any or all of types of dynamic tear testing (particularly recognized types of DT testing, e.g., 1-inch DT testing, ⅜-inch DT testing, etc.) can also be determined in accordance with the present invention.

Notable among the advantages of the inventive nonstandard one-inch DT specimen are the present invention's ability to measure the fracture toughness of small mock-ups or pre-production forgings. Also notable is this invention's ability to measure the fracture toughness of finished forgings without incurring the additional expense of fabricating special forging dies.

Conventionally, for purposes of conducting fracture toughness testing, a special forging die is designed and fabricated to produce excess material from the finished forging. Typically, this excess material is machined from the finish forging and then subjected to fracture toughness tests. It has been the experience of the U.S. Navy that these prolongations may not accurately represent all of the working experienced by the finished product. By comparison, the relatively small test section size of the inventive nonstandard specimen beneficially allows for the testing of the actual forged part.

Mock-ups or pre-production forgings, castings and extrusions are used extensively to screen the effects of different forging/temperature combinations on mechanical properties. The typical small size of the pre-production product precludes the use of the standard 1-inch DT specimen. With inventive acceptance criteria being based on those associated with the standard one-inch DT test, the inventive nonstandard 1-inch DT specimen can be used to accurately gage the effects of various processing combinations on fracture toughness prior to production forging.

Another inventive advantage relates to material savings. The standard one-inch DT specimen is materially intensive. The amount of material required to produce a single standard DT specimen can be used to produce three inventive nonstandard DT specimens—and with some material left over.

Other objects, advantages and features of this invention will become apparent from the following detailed description of the invention when considered in conjunction with the accompanying drawings.

BRIEF DESCRIPTION OF THE APPENDICES

The following appendices are hereby made a part of this disclosure:

Attached hereto marked APPENDIX "A" and incorporated herein by reference is the following aforementioned 22-page U.S. Navy report which discloses various aspects of the standard one-inch DT test: Puzak, P. P. and F. A. Lange, "Standard Method for the 1-inch Dynamic Tear Test," NRL Report 6851, February 1969.

Attached hereto marked APPENDIX "B" and incorporated herein by reference is the following eighteen-page U.S. Navy report which discloses various aspects of the inventive nonstandard one-inch DT test: Wells, Michael E. and Roy A. Lindauer, "A Test Method for Dynamic Tear Testing of Titanium Plate Using a Nonstandard Specimen," CARDIVNSWC-TR-61-97/11, August 1998, Technical Report, Survivability, Structures and Materials Directorate, Carderock Division, Naval Surface Warfare Center, West Bethesda, Md. 20817-5700.

BRIEF DESCRIPTION OF THE DRAWINGS

In order that the present invention may be clearly understood, it will now be described, by way of example, with reference to the accompanying drawings, wherein like numbers indicate the same or similar components, and wherein:

FIG. 5 is a tabular representation of the electron beam welding parameters for the inventive crack-starter weld associated with the two crack-starter grooves shown in FIG. 4A.

FIG. 6A is a diagrammatic plan view of the inventive assembly shown in FIG. 4A, wherein the crack-starter weld is shown provided with notching.

FIG. 6B is a diagrammatic cross-sectional view (medially cross-sectioned in the widthwise direction) of the inventive assembly shown in FIG. 4A, illustrating the trapezoidal configuration of the notching shown in FIG. 6A.

FIG. 8 is a tabular representation, related to FIG. 7A and FIG. 7B, of inventive one-inch dynamic tear results for Ti—6Al—4V plate.

DETAILED DESCRIPTION OF THE INVENTION

The U.S. Navy conducted comparative dynamic tear testing of a standard one-inch dynamic tear specimen and an inventive non-standard one-inch dynamic tear specimen. The commercial grade of titanium alloy Ti—6Al—4V was used in fabrication of both the standard one-inch DT specimen and the inventive nonstandard one-inch DT specimen.

Figures 1A, 1B:
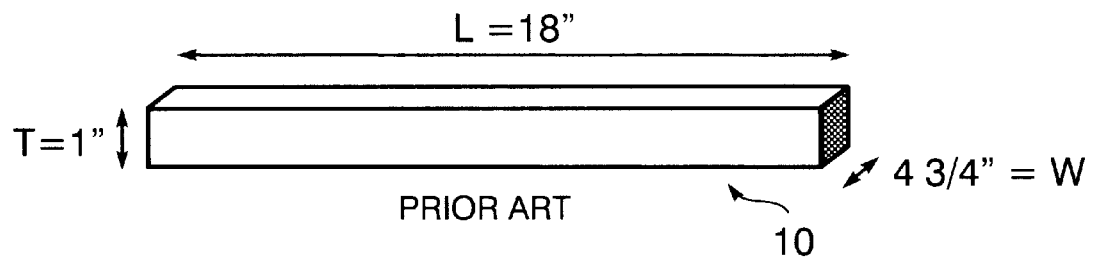
FIG. 1A is a diagrammatic perspective view of a standard one-inch DT specimen blank.
FIG. 1B is a tabular representation of the dimensions (and tolerances) of the standard one-inch DT specimen blank shown in FIG. 1A.

Referring now to FIG. 1A and FIG. 1B, titanium standard one-inch DT specimen blank 10 is characterized by the following approximate dimensions: thickness T=one inch; width W=four and three-fourths inches; length L=eighteen inches. The tolerances for these dimensions are indicated in FIG. 1B.

For purposes of the comparative dynamic tear testing, the U.S. Navy machined four standard one-inch DT specimen blanks from a one-inch thick Ti—6Al—4V plate.

Figures 2A, 2B:
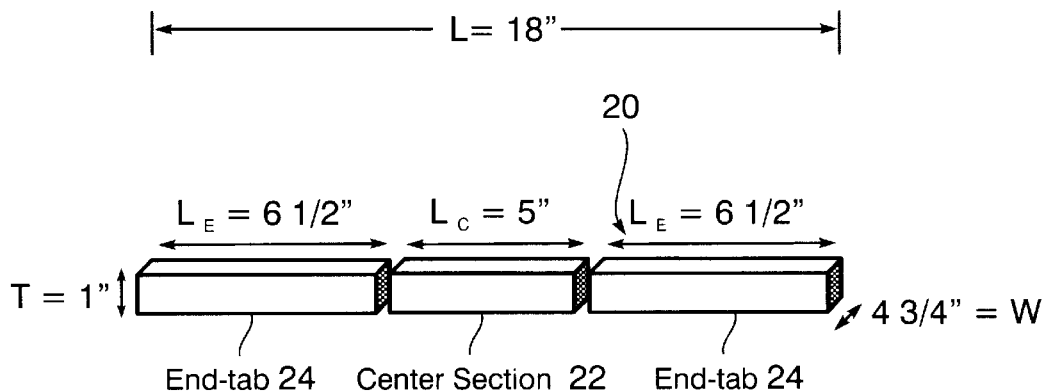
FIG. 2A is a diagrammatic exploded perspective view, similar to the view shown in FIG. 1A, of an unassembled nonstandard one-inch DT specimen blank, including center test section (the non-standard one-inch DT specimen) and two associated end-tabs, in accordance with the present invention.
FIG. 2B is a tabular representation of the dimensions (and tolerances) of the inventive nonstandard one-inch DT specimen blank shown in FIG. 2A.

With reference to FIG. 2A and FIG. 2B, inventive titanium nonstandard one-inch DT specimen blank 20 comprised center section 22 and two end-tabs 24. Center section 22 was the actual "test" section of the nonstandard specimen—i.e., the nonstandard specimen's section for which material properties were being evaluated. The length $L_C$ of center section 22 was five inches. The length $L_E$ of each end-tab 24 was six and one-half inches. Center section 22 and end-tabs 24 each had the same width W (4.75 inches) and thickness T (1 inch) as did standard specimen blank 10.

Thus, the overall dimensions (length L, width W and thickness T) for inventive nonstandard specimen blank 20 equaled the overall dimensions (length L, width W and thickness T) for standard specimen blank 10, viz., length L=18 inches, width W=4.75 inches and thickness T=1 inch. In inventive practice, this dimensional equivalence between standard specimen blank 10 and nonstandard specimen blank 20 permits utilization of the existing dynamic tear testing equipment (normally associated with standard specimens) for testing either standard specimen blank 10 or nonstandard specimen blank 20.

Figures 3A, 3B:
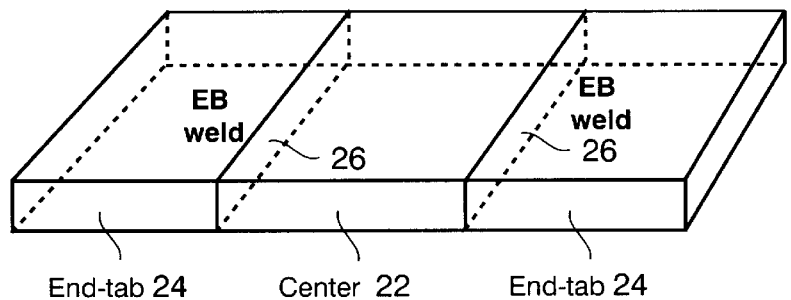
FIG. 3A is a diagrammatic perspective view (different from the view shown in FIG. 2A) of the inventive assembled form of the nonstandard one-inch DT specimen "blank" shown in FIG. 2A, wherein the two end-tabs are shown joined with the center test section.
FIG. 3B is a tabular representation of the electron beam welding parameters for inventively joining the end-tabs to the center test section as shown in FIG. 3A.

Still referring to FIG. 2A and FIG. 2B, and also referring to FIG. 3A and FIG. 3B, nonstandard specimen blank 20 was prepared by joining end-tabs 24 to center section 22 via electron beam (EB) welding. Each end-tab 24 had a side joint surface 26 (one of which is visible in FIG. 2A) which was to adjoin center section 22. In preparation for EB welding, each joint surface 26 was milled to ensure uniform contact, and then cleaned with a degreasing solution.

The U.S. Navy testers: cleaned the two joint surfaces 26 with methyl ethyl ketone (ME); immersed joint surfaces 26 in a room temperature acid enchant consisting of 45 percent nitric acid, 49 percent water and 6 percent turbo 4104 for a period of five to seven minutes; rinsed joint surfaces 26 with tap water; rinsed joint surfaces 26 with distilled water; and, air dried joint surfaces 26.

Reference now being made to FIG. 3A and FIG. 3B, center section 22 and the two end-tabs 24 were aligned in a welding fixture. The EB welding parameters for joining the end-tabs to the center section are provided in FIG. 3B. Center section 22 was positioned with the rolling direction parallel to the width W of the DT specimen. A seal weld was deposited on both sides of each butt joint to maintain alignment. An EB weld was then deposited on the top surface of the square groove. The penetration of the weld was measured as approximately 0.75 inches. The specimen was turned over and another EB weld was deposited on the groove surface to the same depth to ensure complete penetration.

Generally according to practice of this invention, the procedures pertaining to electron beam welding of the crack-starter weld, and to notching of the crack-starter weld, are similar to the corresponding procedures (such as described in APPENDIX A) pertaining to the standard 1-inch DT specimen.

Figures 4A, 4B:
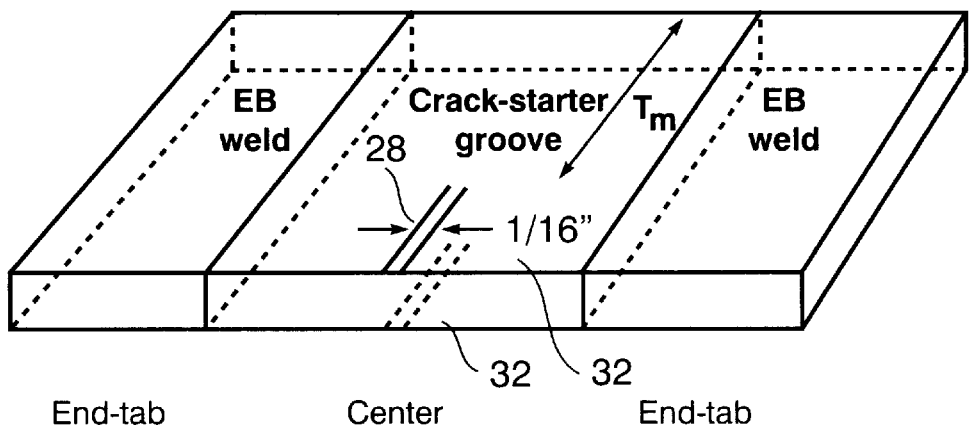
FIG. 4A is a diagrammatic perspective view (different from the view shown in FIG. 3) of the center test section and two associated endtabs shown joined in FIG. 3, wherein two opposite crack-starter grooves are inventively provided in the center test section.
FIG. 4B is a tabular representation of the dimensions (and tolerances) of each inventive crack-starter groove shown in FIG. 4A.

Reference is now made to FIG. 4A, FIG. 4B and FIG. 5 regarding EB welding of crack-starter weld 28. The crack-starter weld was positioned to proved a 3-inch fracture path in the test material $T_m$. Thus, crack-starter weld 28 extended for a length of approximately 1.75 inches. Crack-starter weld 28 was prepared by machining a shallow crack-starter groove 30 along the centerline on each side 32 (upper side and lower, opposite side) of the specimen.

On both the standard and nonstandard specimens, the test material dimension was measured from the compression side and indicated with a marker. A ¹⁄₁₆-inch diameter ball mill was used to cut a 0.062-inch deep crack-starter groove 30 from the tension edge to the mark. The dimensions of crack-starter groove 30 are shown in FIG. 4B for a non-standard DT blank. Generally, the length (in direction of width W) of the crack-starter groove must not be excessive; that is, in inventive practice, the main requirement for this machining procedure is that the crack-starter groove not extend into the test material.

After cleaning the groove with MEK, a clean 1/16-inch diameter steel wire was placed in each machined groove 30 and lightly hammered in place with a center punch. Generally, in inventive practice, any mild steel wire may be used as the embrittling material.

The specimen was aligned in a fixture for EB welding of the steel wire. A seal weld was deposited on both groove surfaces to ensure uniform contact of the steel wire with the titanium base material. An EB weld was then deposited on the surface of one groove. The penetration was measured at approximately 0.80 inches. The specimen was turned over and an EB weld was deposited on the surface of the other groove to the same penetration depth. The parameters for EB welding are provided in FIG. 5.

The crack-starter weld groove 30 on each specimen was notched to assist initiation of the crack in the brittle weld. The notch was prepared by sawing a trapezoid pattern on the tension edge and sides of the crack-starter in accordance with the dimensions provided in Table 6. The tension edge of each specimen was notched first with a 0.062-inch thick saw cut along the centerline of the embrittled EB weld to a depth of 0.25 inches. The specimen was then positioned in an angle vise for saw cutting of the side notches, making sure that the saw cuts did not extend beyond the end of the EB weld into the test material $T_m$.

In inventive practice, the main requirement for notching the crack-starter weld is that the notch be centered on the EB weld and that the side notches do not extend beyond the end of the EB weld. A scribed line, marked 0.125 inches from the end of the EB weld, can be used as a guide to terminate the saw cutting of the side notches. FIG. 1 of APPENDIX B depicts the nonstandard DT specimen including the notched crack-star weld and the welded end-tabs.

All specimens were tested at a test temperature of 30° F.±2° F. the specimens were placed in an insulated container and fully immersed in cold water for a period of one hour. A thermocouple was used to measure the bath temperature. Each specimen was removed from the bath with tongs and placed on the anvil of the test machine.

Figures 7A, 7B:
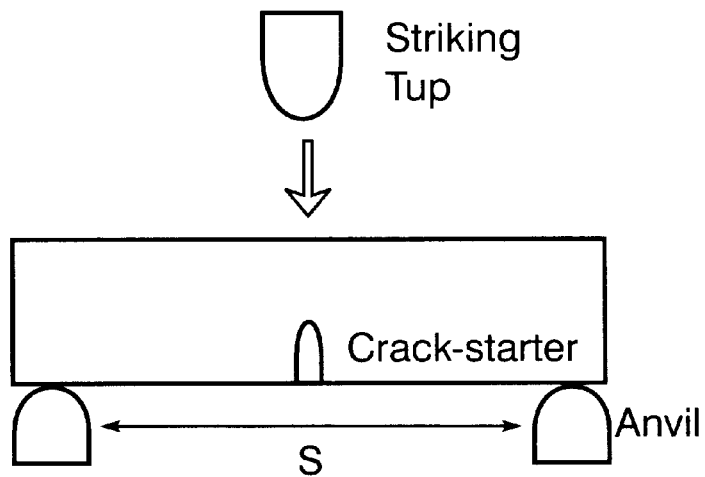
FIG. 7A is a diagrammatic plan view of an embodiment of inventive dynamic tear testing wherein is used a single-pendulum machine.
FIG. 7B is a tabular representation of the specifications for the single-pendulum machine shown in FIG. 7A.

The single-pendulum machine shown in FIG. 2 of APPENDIX B was used for all dynamic tear tests. Referring to FIG. 7A and FIG. 7B, with a maximum vertical drop of 8.872 feet and a hammer weight of 1721.3 pounds, the machine is capable of producing up to 15,272 foot-pounds of energy. Hammer rotation was measured on a laser-etched indicating disk to the nearest 0.1 degree. The machine specifications are provided in FIG. 7B. Each specimen was positioned on the anvil so that the fracture would propagate in the rolling direction of the plate.

Reference is now made to FIG. 8, wherein are provided the test results for both the standard 1-inch DT specimens and the nonstandard 1-inch DT specimens. The range in impact energy for commercial grade Ti—6Al—4V is also provided for comparison. The energy values for the standard specimens ranged from 746 ft-lbs to 841-ft-lbs, with an average value of 790 ft-lbs. The energy values for the nonstandard specimens ranged from 687 ft-lbs to 890 ft-lbs, with an average value of 790 ft-lbs. These results clearly show that the nonstandard specimen accurately measures the fracture energy of Ti—6Al—4V plate material.

Visual examination of the test material surfaces on the nonstandard specimens revealed that the plastic zone extended for a distance of approximately one-half inch. Thus, the 5-inch width of the center section of the specimen was more than adequate for ensuring that all the plastic deformation was contained within this section of the specimen. FIG. 3 of APPENDIX B shows the fracture face of a nonstandard DT specimen, and also illustrates the appearance of the notching details of the crack-starter weld.

The herein described testing performed by the U.S. Navy have demonstrated the adequacy of an inventive nonstandard specimen for measuring the fracture toughness of titanium Ti—6Al—4V plate, in lieu of the standard 1-inch DT specimen. The results of these dynamic tears tests have shown that the nonstandard specimen can be used to accurately measure the fracture energy of this material. Practice of the inventive methodology disclosed herein is recommended for characterization of the fracture toughness properties of alpha-beta titanium alloys in cases of limited material availability.

Figure 9A:
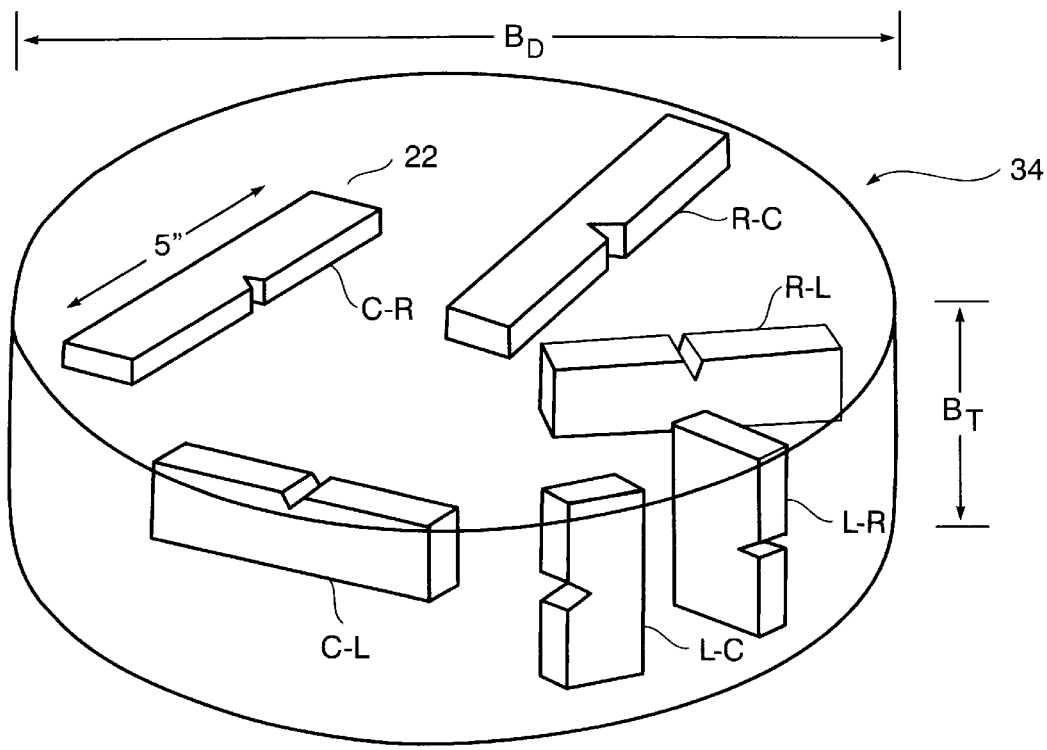
FIG. 9A is a diagrammatic perspective view of a solid cylindrical metallic billet (e.g., a six-inch thick titanium forged billet), illustrating derivation therefrom of variously oriented inventive five-inch center test section blanks.
Figure 9B:
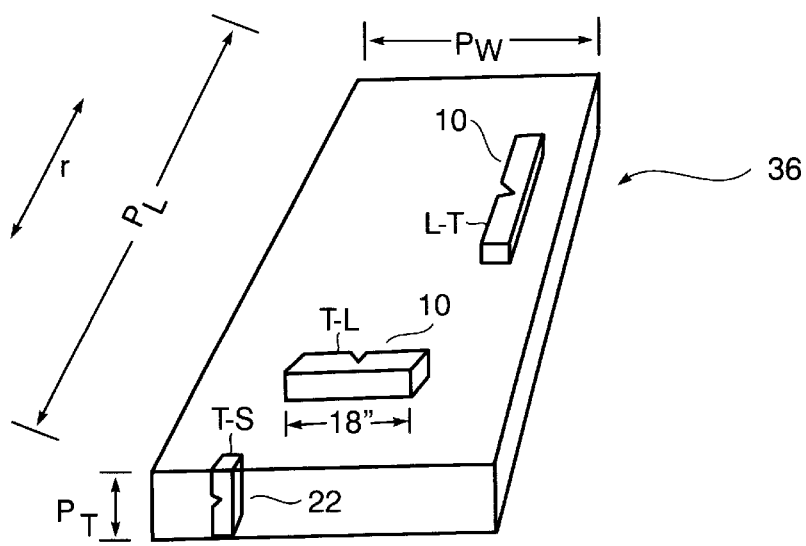
FIG. 9B is a diagrammatic perspective view of a metallic plate or slab, illustrating derivation therefrom of T-L and L-T oriented standard 18-inch long blanks, and T-S oriented inventive nonstandard 5-inch long blanks.

With reference to FIG. 9A and FIG. 9B, many metallic material products are formed to specific shapes. These shapes are diverse both dimensionally and configurationally. Some are rectilinear, some are curvilinear, and some have indicia of both rectilinearity and curvilinearity.

It is seen that the present invention is especially advantageous for "oddly" shaped objects such as forgings, castings, experimental forgings and experimental castings. For instance, it is possible that a metallic dome having a convexly-concavely curved shape would not lend itself to extraction of an 18-inch length standard 1-inch DT test specimen 10, while permitting extraction therefrom of an inventive 18-inch length nonstandard DT specimen 20's 5-inch length center test section 22.

As shown in FIG. 9A, removal (e.g., machining) is possible of the inventive 5-inch center test section 22 in various orientations within the context of the original metallic disk-shaped billet 34. Generally, the material properties of the inventive 5-inch long 1-inch DT test sections 22 taken from a particular piece will vary in accordance with their respective orientations within such piece. The material properties are a function of test direction.

As shown in FIG. 9A, six different orientations of center test section 22 can be tested, viz., circumferential-radial (C-R), radial-circumferential (R-C), radial-longitudinal (R-L), longitudinal-radial (L-R), longitudinal-circumferential (L-C), and circumferential-longitudinal (C-L). A billet 34 such as shown in FIG. 9A, as frequently encountered, is less than 18 inches in diameter $B_D$ but more than 5 inches in thickness BT (e.g., $B_T$=6 inches). For instance, a diametrically less-than-eighteen-inch billet 34 can be used to make a hatch for a marine vessel. It is clear that a billet 34 having a diameter less than 18 inches cannot accommodate a standard 1-inch DT test specimen 10, which is 18 inches long.

By contrast, as shown in FIG. 9B, metallic flat plate material 36 is typically long enough and wide enough (e.g., length $P_L$=6 feet; width $P_W$=12 feet) to accommodate two orientations of an 18-inch long standard 1-inch DT specimen, viz., transverse-longitudinal (T-L) and longitudinal-transverse (L-T); however, regardless of whether an inventive 5-inch long center test section or a standard 18-inch long test specimen is being removed, short-transverse (T-S) orientation frequently cannot be accommodated. That is, many plates 36 cannot be tested "through the thickness" because their thickness $P_T$ is less than 5 inches; typically, a plate's thickness is 4 inches or less). According to this nomenclature, the first letter (e.g., the "L" of "L-T") refers to the orientation of the specimen with respect to rolling direction r; the second letter (e.g., the "T" of "L-T") refers to the direction of the crack propagation with respect to rolling direction r.

Nevertheless, there are thicker plate 36 forms which are sometimes known as "slabs," characterized by a thickness of 5 inches or greater. Such slabs 36 can benefit from the present invention since an inventive 5-inch long center test section can be accommodated when oriented such as shown, thereby enabling through-the-thickness testing of slab 36. The present invention can thus also prove advantageous for thick plates or slabs.

The present invention solves two distinct problems: Firstly, this invention provides for the measurement of DT toughness under circumstances of limited material. Secondly, this invention provides for the generating of (testing for) different properties from the same material entity. The present invention thus advances the efficient, economic and conservative utilization of material resources which are limited for testing purposes.

Especially with regard to the first problem, the present invention allows different material to be used for the end-tabs than is used for the center test section. In the event of unavailability of the same material, but availability of a different (but similar) material, such different material can be inventively used for the end-tabs.

Moreover, especially with regard to the second problem, since the end-tabs are not affected by the inventive methodology, the end-tabs can be used for additional tests. A number of blanks, including center test sections and end-tabs, can be cut out from the same piece. The inventive practitioner can use the end-tabs for inventive DT testing as well as for other kinds of material testing. The blanks which are unaffected by inventive nonstandard DT testing—among which are those used in inventive DT testing as end-tabs, and those not used at all in inventive DT testing—represent specimens testable for properties other than dynamic tear.

The ordinarily skilled artisan is familiar with standard tests for measuring other material properties, including: standard 0.505 tensile tests; Charpy V-notch test (impact toughness); J specimen test (fracture toughness); bend specimen (ductility). These and other conventional tests are standardized by the American Society for Testing and Materials (e.g., ASTM specifications). For the standard 0.505 tensile test and for the Charpy V-notch test, the inventive practitioner can test two orientations, viz., longitudinal and transverse.

The inventive nonstandard specimen for 1-inch dynamic tear tests comprises three pieces, viz., a center test section and two end-tabs. The end-tabs are joined to each side of the center test section by means of electron beam welds. According to many inventive embodiments, the end-tabs are of a different but similar material composition vis-a-vis the center test section, due to limited test material availability.

According to some inventive embodiments, however, the end-tabs are of the same material composition as the center test section. For example, titanium forgings are frequently of a shape wherein the material thickness is less than the 18 inches required for a standard 1-inch DT test, but of a thickness where many inventive smaller blanks (5 inches in length) can be removed. In such cases, the inventive nonstandard specimen can be constructed of material from the same heat or lot. The center test section can be used to measure 1-inch DT toughness. The end-tabs can be removed after DT testing for additional mechanical property characterization. The length and thickness of the inventive end-tabs are sufficient to accommodate standard 0.505 tensile specimens in both the LT (longitudinal-transverse) and TL (transverse-longitudinal) orientations, Charpy V-notch specimens in both test directions, bend specimens, and other potential specimens for mechanical property testing.

Therefore, in accordance with the present invention, it is not necessary that the end-tabs be made of the same material as the center test section is made of. Nor is it necessary in inventive practice that the end-tabs be made of the same product form as the center test section is made of. For instance, plate end-tabs of composition A can be inventively implemented in association with a forged or cast center test section of composition B. Or, forged or cast end-tabs of composition A can be inventively implemented in association with a plate center test section of composition B. In fact, it is not even inventively necessary that the end-tabs themselves be made of the same material; nor is it necessary that the end-tabs themselves be made of the same product form. For instance, a plate end-tab of composition A can be inventively implemented in association with a forged end-tab of composition B and a cast center test section of composition C.

Figures 6C, 10:
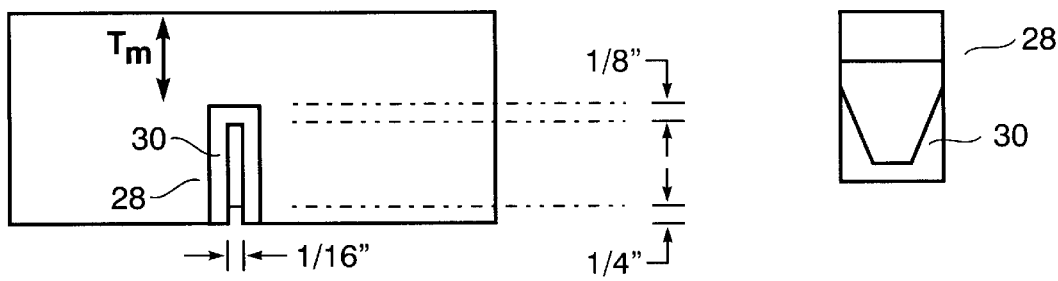
FIG. 6C is a tabular representation of the dimensions (and tolerances) of the inventive notched crack-starter shown in FIG. 6A.
FIG. 10 is a tabular representation of the length of the inventive center test section as a function of titanium groupings.

The length of the center test section is designed to encompass all of the plastic deformation that the specimen undergoes during impact testing. A center test section length of five (5) inches is expected to encompass the plastic deformation for all titanium alloys commercially available. With reference to FIG. 10, the length of the center test section can be reduced as a function of the material grouping. Titanium and titanium alloys are commonly grouped as follows:

Unalloyed or commercially pure

Alpha and near alpha

Alpha-beta

Beta

Generally, the unalloyed or commercially pure grades have the lowest strength and highest impact toughness. The beta alloys have the highest strength and lowest fracture toughness. As the strength level increases the zone of plastic deformation in the center test section decreases. Hence, the length of the center test section can be reduced as the strength level increases. The length of the center test section as a function of the titanium groupings is shown in FIG. 10.

With reference to FIG. 10, in accordance with the present invention, a center test section made of a material in the unalloyed or commercially pure group of titanium alloy should have a length of no less than five inches. A center test section made of a material in the alpha and near alpha group of titanium alloy should have a length of no less than four inches. A center test section made of a material in the alpha-beta group of titanium alloy should have a length of no less than three inches. A center test section made of a material in the beta group of titanium alloy should have a length of no less than two inches. As pertains to each group, the indicated center test section length represents the minimum center test section length which will assure complete encompassment of the plastic deformation of such center test section.

Figure 11:
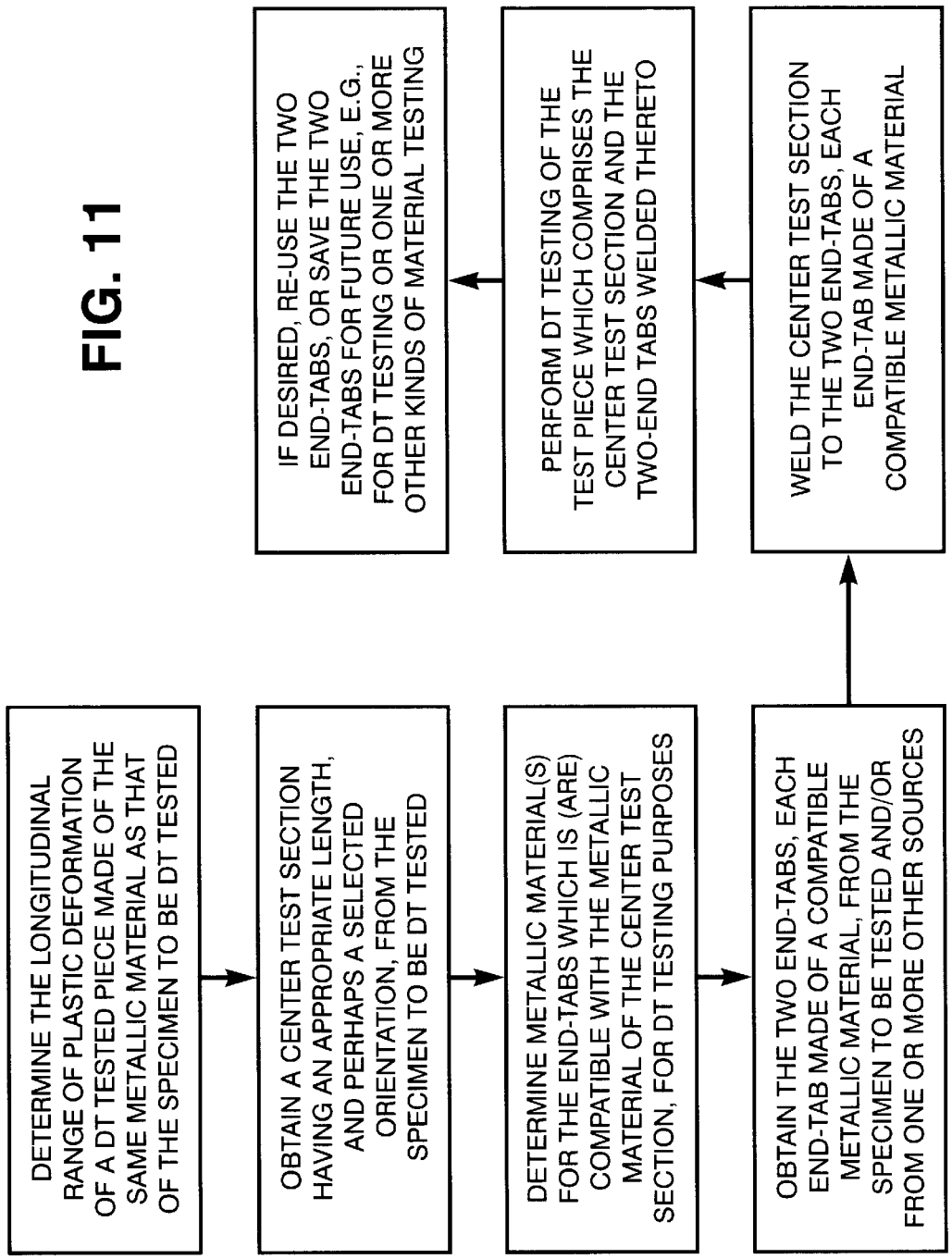
FIG. 11 is a flow diagram illustrating typical steps that would be performed for practicing the present invention.

Reference is now made to FIG. 11 through FIG. 15. As shown in FIG. 11, typically first among the steps which an inventive practitioner will take is the determination of the extent of plastic deformation of a particular type of metallic material. The inventive practitioner thus ascertains the shortest possible length of a center test section 22 that he can extract from an object—that is, the minimum center test section 22 length $L_C$ which is completely viable for purposes of being subjected to DT testing.

Figure 12:
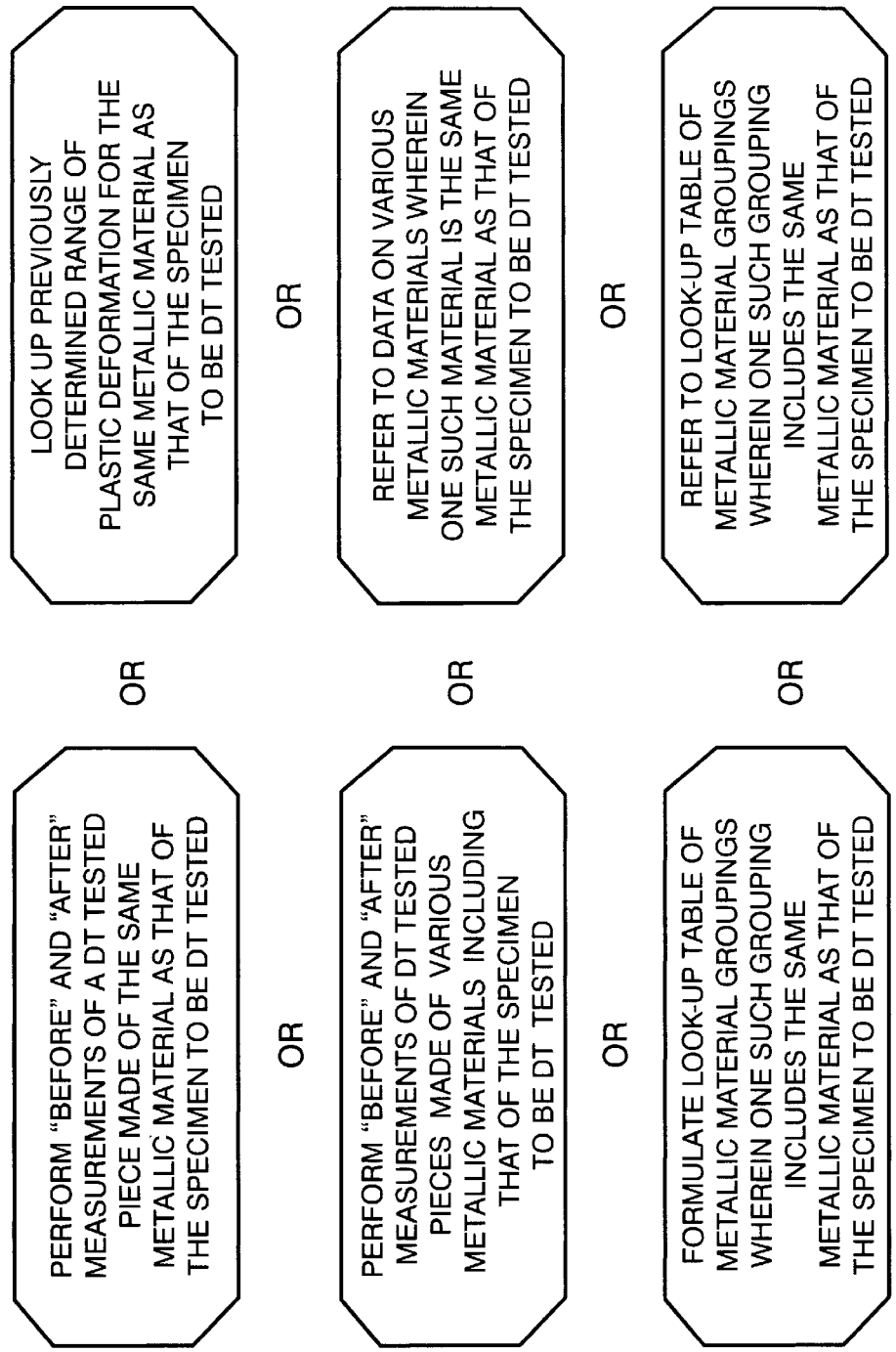
FIG. 12 is a block diagram illustrating various ways in which the expected longitudinal range of plastic deformation of a DT test piece made of a particular metallic material can be determined in accordance with the present invention.
Figure 13:
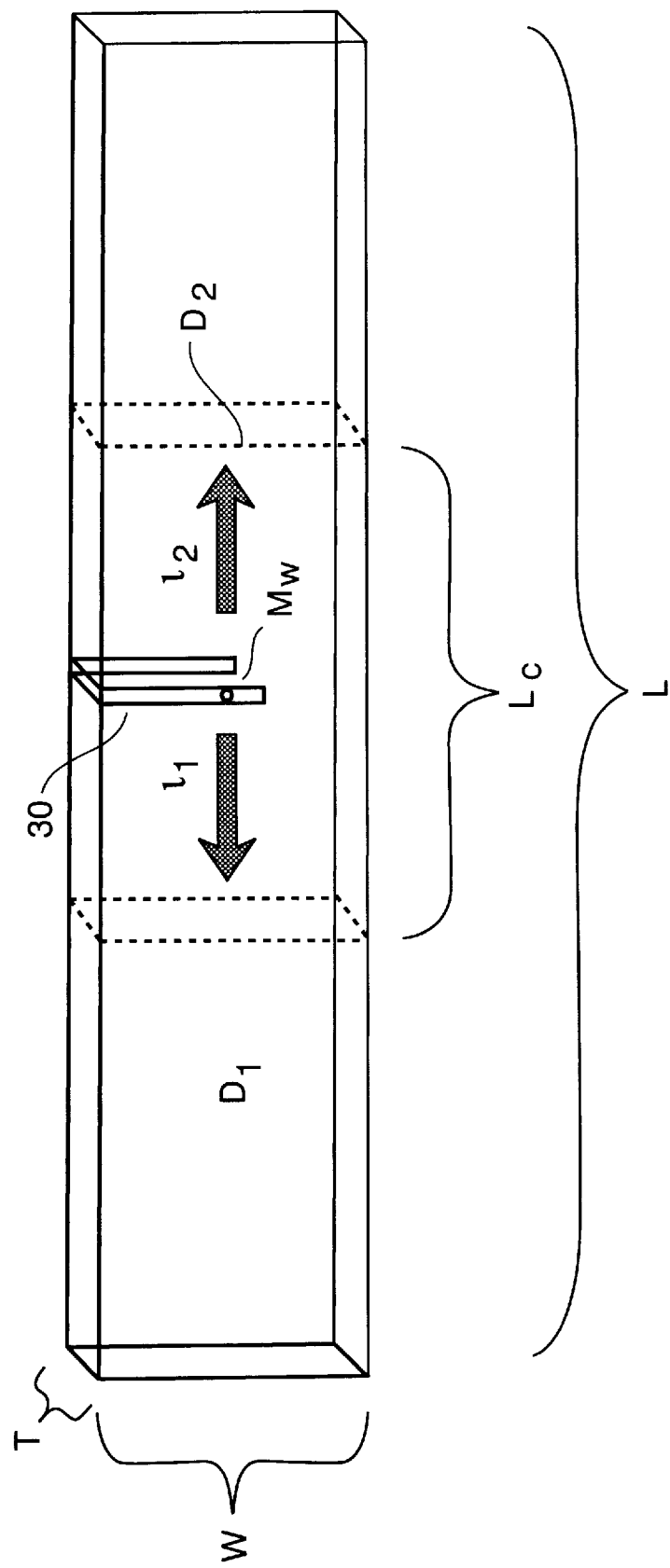
FIG. 13 is a diagrammatic perspective view of a standard eighteen-inch long, one-inch thick DT test piece, illustrating how the longitudinal range of plastic deformation of a DT test piece made of a particular metallic material can be empirically ascertained.

As represented in FIG. 12, this determination of plastic deformation range can be made in any of a number of ways. According to some approaches, the inventive practioner can refer to data which he or another has already generated. In this regard, as previously described herein with reference to FIG. 10, inventive guidelines have been formulated pertaining to one-inch DT testing of metallic test materials made of titanium or titanium alloy. The length of center test section 22 (i.e., the extent of plastic deformation) depends upon which of the four titanium/titanium alloy subcategories (viz:, unalloyed grades, alpha and near alpha alloys, alpha-beta alloys and beta alloys) encompasses the subject titanium/titanium alloy material.

Similar guidelines can be inventively ascertained "in the lab" as to classes of metallic materials beside titanium and titanium alloys, such as the following: iron and iron alloys; aluminum and aluminum alloys; copper and copper alloys; and, nickel and nickel alloys. The inventive practitioner himself can perform "before" and "after" measurements, such as as portrayed in FIG. 13 and previously described herein. For instance, referring to FIG. 13, the 4.75 inch width W and one-inch thickness T of a standard one-inch DT test specimen blank 10 having eighteen-inch length L is initially measured (presumably, confirmed with exactitude to uniformly be W≈4.75 inches and T≈1 inch). Then, the standard DT test piece 10 is subjected to standard one-inch DT testing. Then, the width W and thickness T of the standard eighteen-inch length DT test piece 10 are measured again. In particular, on each occasion the thickness T is measured starting from the widthwise midpoint $M_W$ of the fracture edge of crack-starter groove 30 and proceeding in opposite lengthwise directions $l_1$ and $l_2$.

Such measurements can be performed on an ad hoc basis, or for purposes of producing guidelines for subclasses within a particular class of metallic material in relation to a particular form of dynamic tear testing. As discussed hereinabove, FIG. 10 exemplifies such inventive guidelines in relation to titanium and titanium alloys and one-inch DT testing therof. It is emphasized that the principles of this invention are applicable not only to one-inch dynamic tear testing but also to other forms of dynamic tear testing, whether standardized or non-standardized.

The thickness T of the test piece prior to being subjected to standard DT testing, which will normally be constant, is compared to the thickness T of the test piece subsequent to being subjected to standard DT testing, which will normally be nonconstant (e.g., graduated). Within the range of plastic deformation, the post-test thickness T differs from (typically, is less than) the pre-test thickness T. The extreme demarcations $D_1$ and $D_2$ of plastic deformation correspond to the locations at which the the post-test thickness ceases to differ from the pre-test thickness, i.e., where they are equal. The longitudinal distance $L_C$ is the minimum inventively practical length of a center test section made of the subject material.

Figure 14:
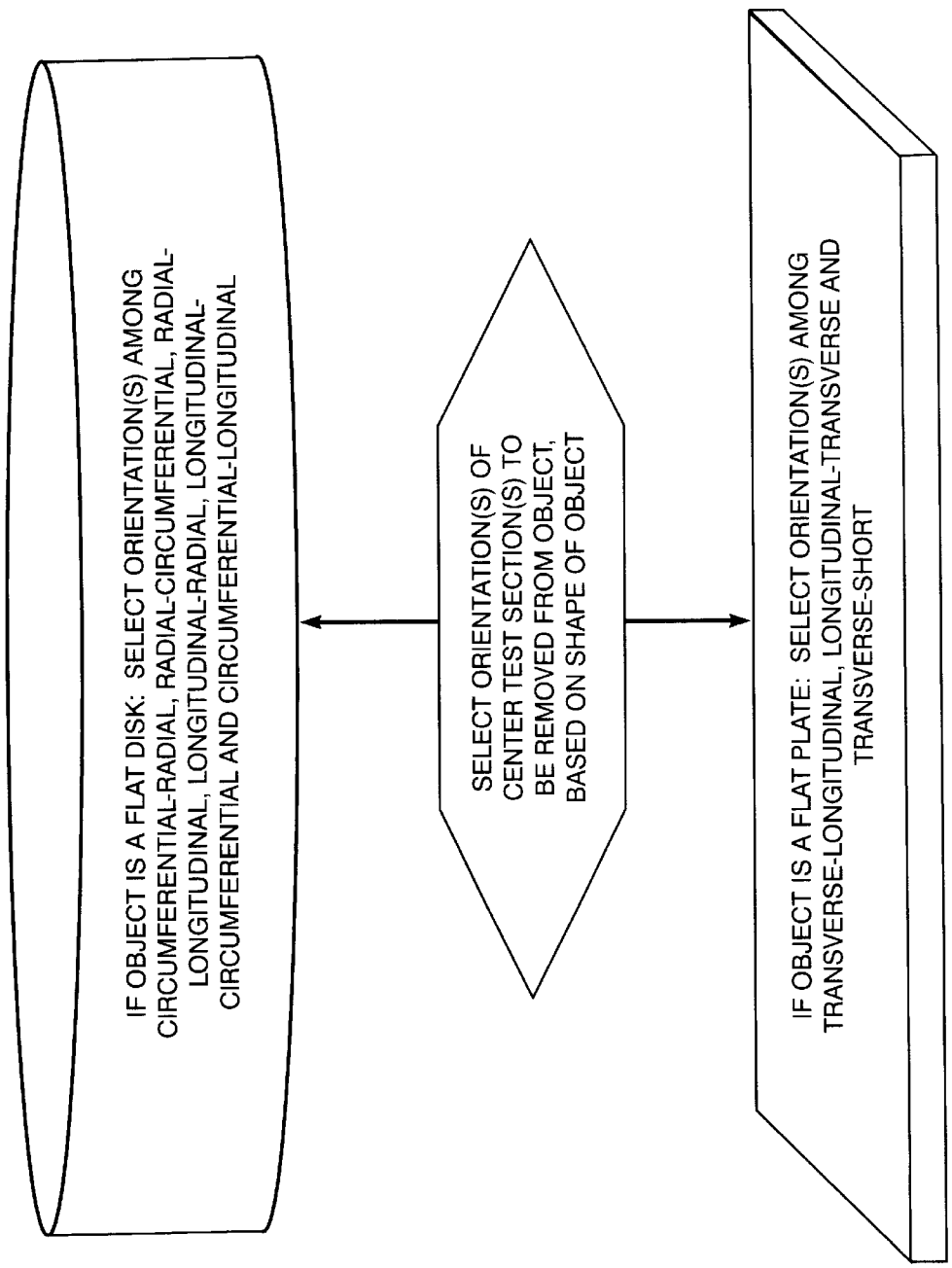
FIG. 14 is a block diagram illustrating how, in accordance with the present invention, the removal of one or more center test sections from an object can be accomplished by selecting one or more various orientations of such center test section or sections, such orientations depending on the shape of the object.
Figure 15:
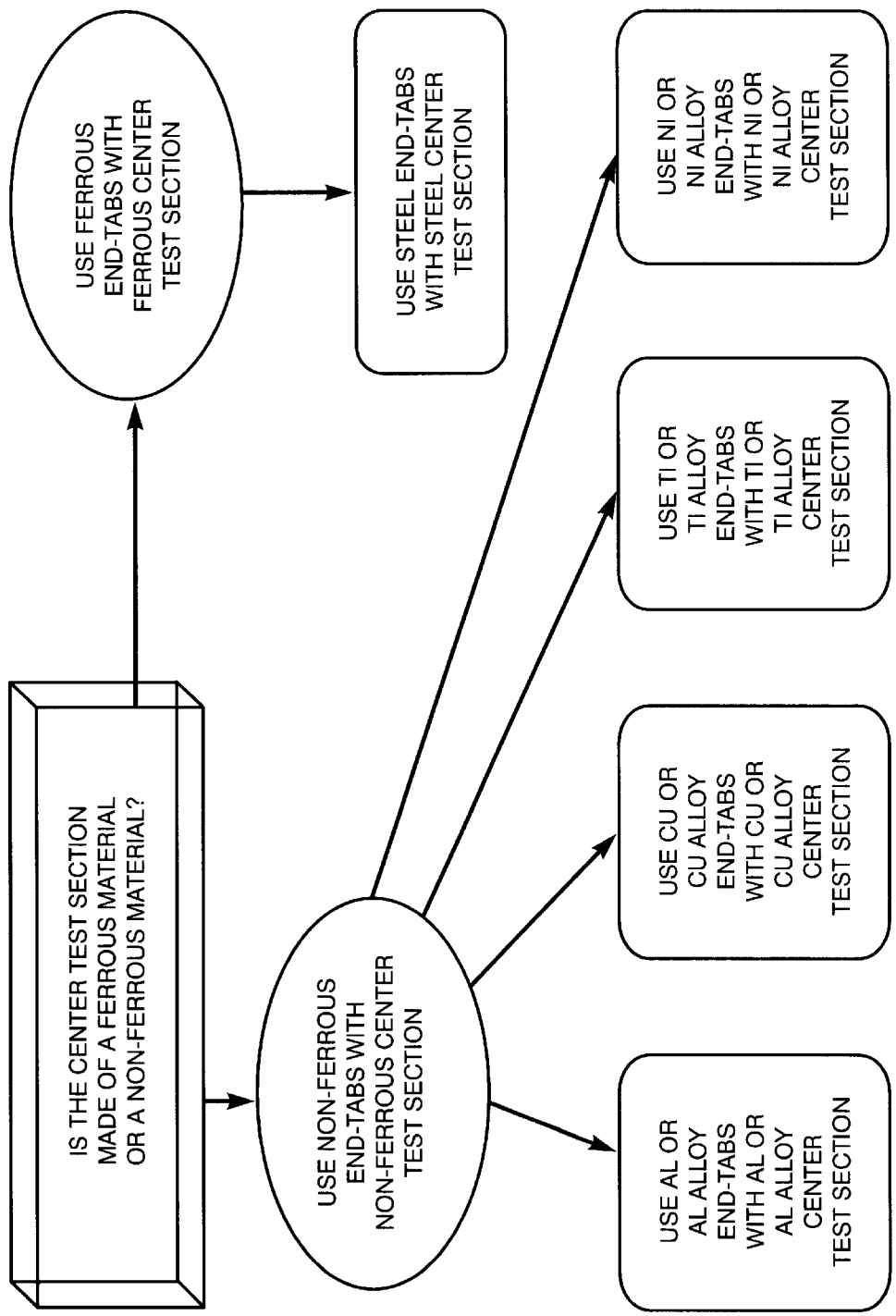
FIG. 15 is a block diagram illustrating how compatibility of end-tab materials with a center test section material is determined in accordance with the present invention.

As pertains to inventive extraction of a center test section 22 from variously shaped objects, objects of certain shapes lend themselves to DT testing based on orientations of the center test sections 10 within such objects. For instance, as previously discussed herein with reference to FIG. 9A and FIG. 9B and as depicted in FIG. 14, disk-shaped objects 34 and flat planar objects 36 can each be analysed in terms of dynamic tear properties (and other material properties) exhibited in correspondence with different orientations of the inventive center test sections extracted therefrom.

Once a center test section 22 of appropriate length is taken from an object, the inventive center test section 22 will be joined at the ends by two inventive end-tabs 24, e.g., by means of a welding procedure. Now referring to FIG. 15, an inventive "rule of thumb" is that ferrous end-tabs 24 are to be joined with a ferrous center test section 22, and non-ferrous end-tabs 24 are to be joined with a non-ferrous center test section 22. A ferrous material is iron or an iron alloy. A more typically utilized ferrous material than iron would be an alloy of iron such as steel. There is greater diversity among the non-ferrous materials than among the ferrous materials.

In this regard, a further inventive guideline pertains to center test sections 22 made of non-ferrous materials. Within the realm of non-ferrous materials are four categories, viz., (i) aluminum or aluminum alloy, (ii) copper or copper alloy, (iii) titanium or titanium alloy, and (iv) nickel or nickel alloy. Hence, when center test section 22 is non-ferrous, the practitioner must additionally consider which of these categories of non-ferrous materials includes the non-ferrous material of which center test section 22 is made. For purposes of being welded together according to this invention, non-ferrous center test section 22 and non-ferrous end-tabs 24 must all fall under the same category of non-ferrous materials.

That is, aluminum or aluminum alloy end-tabs 24 must be used with an aluminum or aluminum alloy center test section 22. Copper or copper alloy end-tabs 24 must be used with a copper or copper alloy center test section 22. Titanium or titanium alloy end-tabs 24 must be used with a titanium or titanium alloy center test section 22. Nickel or nickel alloy end-tabs 24 must be used with a nickel or nickel alloy center test section 22.

The invention requires that the center test section 22 and end-tabs 24 be included within the same metallic material category; however, the invention does not require that the center test section 22 and end-tabs 24 all be made of the same material within such category. For instance, same or different grades of steel can be used for one, two or all three pieces among center test section 22 and end-tabs 24. As another example, same or different subcategories of titanium/titanium alloys—i.e., selected among unalloyed grades, alpha and near alpha alloys, alpha-beta alloys and beta alloys—can be used for one, two or all three pieces among center test section 22 and end-tabs 24.

Other embodiments of this invention will be apparent to those skilled in the art from a consideration of this specification or practice of the invention disclosed herein. Various omissions, modifications and changes to the principles described may be made by one skilled in the art without departing from the true scope and spirit of the invention which is indicated by the following claims.

What is claimed is:

1. A method for obtaining a rectangular parallelepiped section from an object for the purpose of being subjected to dynamic tear testing of the kind wherein a rectangular parallelepiped specimen made of a metallic material is impacted, wherein said specimen has a prescribed length, a prescribed width and a prescribed thickness, and wherein said specimen has provided therein a crack through said thickness and a portion of said width for initiating fracture of said specimen when impacted, said method comprising:
    determining the extent of lengthwise plastic deformation of said specimen which would result if said specimen were subjected to said dynamic tear testing; and obtaining from said object said rectangular parallelepiped section having said prescribed width, said prescribed thickness and a nonprescribed length which is shorter than said prescribed length, said nonprescribed length being at least as great as said determined extent of lengthwise plastic deformation.

2. A method as recited in claim 1, wherein:

said dynamic tear testing is one-inch dynamic tear testing;

said prescribed length is eighteen inches;

said prescribed width is four and three-quarters inches;

said prescribed thickness is one inch; and said nonprescribed length is no greater than five inches.

3. A method as recited in claim 2, wherein, said metallic material is one of titanium and titanium alloy.

4. A method as recited in claim 3, wherein:

said metallic material is selected from the group consisting of unalloyed titanium, commercially pure titanium, alpha titanium alloy, near alpha titanium alloy, alpha-beta titanium alloy and beta titanium alloy;

if said metallic material is unalloyed titanium, said nonprescribed length is no greater than five inches;

if said metallic material is commercially pure titanium, said nonprescribed length is no greater than five inches;

if said metallic material is alpha titanium alloy, said nonprescribed length is no greater than four inches;

if said metallic material is near alpha titanium alloy, said nonprescribed length is no greater than four inches;

if said metallic material is alpha-beta titanium alloy, said nonprescribed length is no greater than three inches; and if said metallic material is beta titanium alloy, said nonprescribed length is no greater than two inches.

5. A method as recited in claim 1, wherein said determining the extent includes referring to data pertaining to the extent of lengthwise plastic deformation which would result when an exemplary said specimen made of the same metallic material of which said object is made were subjected to said dynamic tear testing.

6. A method as recited in claim 1, wherein said determining the extent includes referring to data pertaining to the extent of lengthwise plastic deformation which would result when an exemplary said specimen made of a metallic material belonging to same subcategory of the same category of metallic material of which said object is made were subjected to said dynamic tear testing.

7. A method as recited in claim 1, wherein said determining the extent includes:

subjecting to said dynamic tear testing an exemplary specimen which is made of the same metallic material of which said object is made; and measuring the extent of lengthwise plastic deformation of said exemplary specimen.

8. A method as recited in claim 1, wherein said determining the extent includes formulating data pertaining to the extent of lengthwise plastic deformation which would result when exemplary specimens made of of metallic materials belonging to at least one subcategory of the same category of metallic material of which said object is made were subjected to said dynamic tear testing, said formulating data including:

subjecting to said dynamic tear testing at least one said exemplary specimen, wherein at least one said exemplary specimen belongs to the same subcategory of the same category of metallic material of which said object is made; and measuring the extent of lengthwise plastic deformation of each said exemplary specimen.

9. A method as recited in claim 1, wherein said object is disk-shaped, and wherein said obtaining from said object includes extracting said rectangular parallelepiped section having an orientation, in the context of said object, selected from the group of orientations consisting of circumferential-radial, radial-circumferential, radial-longitudinal, longitudinal-radial, longitudinal-circumferential and circumferential-longitudinal.

10. A method as recited in claim 1, wherein said object is plate-shaped, and wherein said obtaining from said object includes extracting said rectangular parallelepiped section having an orientation, in the context of said object, selected from the group of orientations consisting of transverse-longitudinal, longitudinal-transverse and short-transverse.

11. A method for making a rectangular parallepiped integral entity to be used for the purpose of performing, in relation to an object, dynamic tear testing of the kind wherein a rectangular parallepiped specimen made of a metallic material is impacted, said specimen having a prescribed length, a prescribed width and a prescribed thickness, said specimen having provided therein a crack through said thickness and along a portion of said width for initiating fracture of said specimen when impacted, said method comprising:

determining the extent of lengthwise plastic deformation of said specimen which would result if said specimen were subjected to said dynamic tear testing;

obtaining from said object a rectangular parallelepiped section having said prescribed width, said prescribed thickness and a section length which is shorter than said prescribed length, said section length being at least as great as said determined extent of lengthwise plastic deformation; and joining at lengthwise opposite ends of said section a pair of congruent rectangular parallelepiped end-tabs, each said end-tab having said prescribed width, said prescribed thickness and an end-tab length which is equal to one-half the difference between said prescribed length and said section length, thereby forming said integral entity having said prescribed length, said prescribed width and said prescribed thickness, said integral entity being adaptable to being used as said specimen for said purpose.

12. A method as recited in claim 11, wherein:

said dynamic tear testing is one-inch dynamic tear testing;

said prescribed length is eighteen inches;

said prescribed width is four and three-quarters inches;

said prescribed thickness is one inch; and said nonprescribed length is no greater than five inches.

13. A method as recited in claim 12, wherein:

said metallic material is one of titanium and titanium alloy;

said metallic material is selected from the group consisting of unalloyed titanium, commercially pure titanium, alpha titanium alloy, near alpha titanium alloy, alpha-beta titanium alloy and beta titanium alloy;

if said metallic material is unalloyed titanium, said nonprescribed length is no greater than five inches;

if said metallic material is commercially pure titanium, said nonprescribed length is no greater than five inches;

if said metallic material is alpha titanium alloy, said nonprescribed length is no greater than four inches;

if said metallic material is near alpha titanium alloy, said nonprescribed length is no greater than four inches;

if said metallic material is alpha-beta titanium alloy, said nonprescribed length is no greater than three inches; and if said metallic material is beta titanium alloy, said nonprescribed length is no greater than two inches.

14. A method for making a rectangular parallepiped integral entity to be used for the purpose of performing, in relation to an object, dynamic tear testing of the kind wherein a rectangular parallepiped specimen made of a metallic material is impacted, said specimen having a prescribed length, a prescribed width and a prescribed thickness, said specimen having provided therein a crack through said thickness and along a portion of said width for initiating fracture of said specimen when impacted, said method comprising:

determining the extent of lengthwise plastic deformation of said specimen which would result if said specimen were subjected to said dynamic tear testing;

obtaining from said object a rectangular parallelepiped section having said prescribed width, said prescribed thickness and a section length which is shorter than said prescribed length, said section length being at least as great as said determined extent of lengthwise plastic deformation; and joining at lengthwise opposite ends of said section a pair of congruent rectangular parallelepiped end-tabs, each said end-tab having said prescribed width, said prescribed thickness and an end-tab length which is equal to one-half the difference between said prescribed length and said section length, thereby forming said integral entity having said prescribed length, said prescribed width and said prescribed thickness, said integral entity being adaptable to being used as said specimen for said purpose;

wherein said determining the extent includes at least one of the following:
  (a) referring to data pertaining to the extent of lengthwise plastic deformation which would result when an exemplary said specimen made of the same metallic material of which said object is made were subjected to said dynamic tear testing;
  (b) referring to data pertaining to the extent of lengthwise plastic deformation which would result when an exemplary said specimen made of a metallic material belonging to same subcategory of the same category of metallic material of which said object is made were subjected to said dynamic tear testing;
  (c) subjecting to said dynamic tear testing an exemplary specimen which is made of the same metallic material of which said object is made, and measuring the extent of lengthwise plastic deformation of said exemplary specimen; and
  (d) formulating data pertaining to the extent of lengthwise plastic deformation which would result when exemplary specimens made of metallic materials belonging to at least one subcategory of the same category of metallic material of which said object is made were subjected to said dynamic tear testing, said formulating data including subjecting to said dynamic tear testing at least one said exemplary specimen, wherein at least one said exemplary specimen belongs to the same subcategory of the same category of metallic material of which said object is made, and measuring the extent of lengthwise plastic deformation of each said exemplary specimen.

15. A method as recited in claim 11, wherein:

if said object is disk-shaped, said obtaining from said object includes extracting said rectangular parallelepiped section having an orientation, in the context of said object, selected from the group of orientations consisting of circumferential-radial, radial-circumferential, radial-longitudinal, longitudinal-radial, longitudinal-circumferential and circumferential-longitudinal; and if said object is plate-shaped, said obtaining from said object includes extracting said rectangular parallelepiped section having an orientation, in the context of said object, selected from the group of orientations consisting of transverse-longitudinal, longitudinal-transverse and short-transverse.

16. A method as recited in claim 11, wherein said joining includes welding said end-tabs to said section.

17. A method as recited in claim 11, further comprising selecting said end-tabs based on their material compatibility with respect to said section, wherein:

a ferrous end-tab is compatible with a ferrous said section;

a ferrous end-tab is incompatible with a non-ferrous said section;

a non-ferrous end-tab is incompatible with a ferrous said section;

a non-ferrous end-tab made of either of aluminum and aluminum alloy is compatible with a non-ferrous section made of either of aluminum and aluminum alloy;

a non-ferrous end-tab made of either of copper and copper alloy is compatible with a non-ferrous section made of either of copper and copper alloy;

a non-ferrous end-tab made of one of titanium and titanium alloy is compatible with a section made of either of titanium and titanium alloy;

a non-ferrous end-tab made of either of nickel and nickel alloy is compatible with a non-ferrous section made of either of nickel and nickel alloy;

a non-ferrous end-tab made of either of aluminum and aluminum alloy is incompatible with a non-ferrous section made of any of copper, copper alloy, titanium, titanium alloy, nickel and nickel alloy;

a non-ferrous end-tab made of either of copper and copper alloy is incompatible with a non-ferrous section made of any of aluminum, aluminum alloy, titanium, titanium alloy, nickel and nickel alloy;

a non-ferrous end-tab made of either of titanium and titanium alloy is incompatible with a non-ferrous section made of any of aluminum, aluminum alloy, copper, copper alloy, nickel and nickel alloy;

a non-ferrous end-tab made of either of nickel and nickel alloy is incompatible with a non-ferrous section made of any of aluminum, aluminum alloy, copper, copper alloy, titanium and titanium alloy;

a non-ferrous section made of either of aluminum and aluminum alloy is incompatible with a non-ferrous end-tab made of any of copper, copper alloy, titanium, titanium alloy, nickel and nickel alloy;

a non-ferrous section made of either of copper and copper alloy is incompatible with a non-ferrous end-tab made of any of aluminum, aluminum alloy, titanium, titanium alloy, nickel and nickel alloy;

a non-ferrous section made of either of titanium and titanium alloy is incompatible with a non-ferrous end-tab made of any of aluminum, aluminum alloy, copper, copper alloy, nickel and nickel alloy; and a non-ferrous section made of either of nickel and nickel alloy is incompatible with a non-ferrous end-tab made of any of aluminum, aluminum alloy, copper, copper alloy, titanium and titanium alloy.

18. A method for performing, in relation to an object, dynamic tear testing of the kind wherein a rectangular parallelepiped specimen made of a metallic material is impacted, said specimen having a prescribed length, a prescribed width and a prescribed thickness, said specimen having provided therein a crack through said thickness and along a portion of said width for initiating fracture of said specimen when an impact is caused with respect thereto, said method comprising:

determining the extent of lengthwise plastic deformation of said specimen which would result if said specimen were subjected to said dynamic tear testing;

obtaining from said object a rectangular parallelepiped section having said prescribed width, said prescribed thickness and a section length which is shorter than said prescribed length, said section length being at least as great as said determined extent of lengthwise plastic deformation;

joining at lengthwise opposite ends of said section a pair of congruent rectangular parallelepiped end-tabs, each said end-tab having said prescribed width, said prescribed thickness and an end-tab length which is equal to one-half the difference between said prescribed length and said section length, thereby forming said integral entity having said prescribed length, said prescribed width and said prescribed thickness, said integral entity being adaptable to being used as said specimen for said performing of said dynamic tear testing;

providing said crack in said integral entity; and causing said impact with respect to said integral entity.

19. A method as recited in claim 18, wherein:

said dynamic tear testing is one-inch dynamic tear testing;

said prescribed length is eighteen inches;

said prescribed width is four and three-quarters inches;

said prescribed thickness is one inch; and said nonprescribed length is no greater than five inches.

20. A method as recited in claim 19, wherein:

said metallic material is one of titanium and titanium alloy;

said metallic material is selected from the group consisting of unalloyed titanium, commercially pure titanium, alpha titanium alloy, near alpha titanium alloy, alpha-beta titanium alloy and beta titanium alloy;

if said metallic material is unalloyed titanium, said nonprescribed length is no greater than five inches;

if said metallic material is commercially pure titanium, said nonprescribed length is no greater than five inches;

if said metallic material is alpha titanium alloy, said nonprescribed length is no greater than four inches;

if said metallic material is near alpha titanium alloy, said nonprescribed length is no greater than four inches;

if said metallic material is alpha-beta titanium alloy, said nonprescribed length is no greater than three inches; and if said metallic material is beta titanium alloy, said nonprescribed length is no greater than two inches.

21. A method for performing, in relation to an object, dynamic tear testing of the kind wherein a rectangular parallelepiped specimen made of a metallic material is impacted, said specimen having a prescribed length, a prescribed width and a prescribed thickness, said specimen having provided therein a crack through said thickness and along a portion of said width for initiating fracture of said specimen when an impact is caused with respect thereto, said method comprising:

determining the extent of lengthwise plastic deformation of said specimen which would result if said specimen were subjected to said dynamic tear testing;

obtaining from said object a rectangular parallelepiped section having said prescribed width, said prescribed thickness and a section length which is shorter than said prescribed length, said section length being at least as great as said determined extent of lengthwise plastic deformation;

joining at lengthwise opposite ends of said section a pair of congruent rectangular parallelepiped end-tabs, each said end-tab having said prescribed width, said prescribed thickness and an end-tab length which is equal to one-half the difference between said prescribed length and said section length, thereby forming said integral entity having said prescribed length, said prescribed width and said prescribed thickness, said integral entity being adaptable to being used as said specimen for said performing of said dynamic tear testing;

providing said crack in said integral entity; and causing said impact with respect to said integral entity;

wherein said determining the extent includes at least one of the following:

(a) referring to data pertaining to the extent of lengthwise plastic deformation which would result when an exemplary said specimen made of the same metallic material of which said object is made were subjected to said dynamic tear testing;

(b) referring to data pertaining to the extent of lengthwise plastic deformation which would result when an exemplary said specimen made of a metallic material belonging to same subcategory of the same category of metallic material of which said object is made were subjected to said dynamic tear testing;

(c) subjecting to said dynamic tear testing an exemplary specimen which is made of the same metallic material of which said object is made, and measuring the extent of lengthwise plastic deformation of said exemplary specimen; and (d) formulating data pertaining to the extent of lengthwise plastic deformation which would result when exemplary specimens made of metallic materials belonging to at least one subcategory of the same category of metallic material of which said object is made were subjected to said dynamic tear testing, said formulating data including subjecting to said dynamic tear testing at least one said exemplary specimen, wherein at least one said exemplary specimen belongs to the same subcategory of the same category of metallic material of which said object is made, and measuring the extent of lengthwise plastic deformation of each said exemplary specimen.

22. A method as recited in claim 18, wherein:

if said object is disk-shaped, said obtaining from said object includes extracting said rectangular parallelepiped section having an orientation, in the context of said object, selected from the group of orientations consisting of circumferential-radial, radial-circumferential, radial-longitudinal, longitudinal-radial, longitudinal-circumferential and circumferential-longitudinal; and if said object is plate-shaped, said obtaining from said object includes extracting said rectangular parallelepiped section having an orientation, in the context of said object, selected from the group of orientations consisting of transverse-longitudinal, longitudinal-transverse and short-transverse.

23. A method as recited in claim 18, wherein said joining includes welding said end-tabs to said section.

24. A method as recited in claim 18, further comprising selecting said end-tabs based on their material compatibility with respect to said section, wherein:

- a ferrous end-tab is compatible with a ferrous said section;
- a ferrous end-tab is incompatible with a non-ferrous said section;
- a non-ferrous end-tab is incompatible with a ferrous said section;
- a non-ferrous end-tab made of either of aluminum and aluminum alloy is compatible with a non-ferrous section made of either of aluminum and aluminum alloy;
- a non-ferrous end-tab made of either of copper and copper alloy is compatible with a non-ferrous section made of either of copper and copper alloy;
- a non-ferrous end-tab made of one of titanium and titanium alloy is compatible with a section made of either of titanium and titanium alloy;
- a non-ferrous end-tab made of either of nickel and nickel alloy is compatible with a non-ferrous section made of either of nickel and nickel alloy;
- a non-ferrous end-tab made of either of aluminum and aluminum alloy is incompatible with a non-ferrous section made of any of copper, copper alloy, titanium, titanium alloy, nickel and nickel alloy;
- a non-ferrous end-tab made of either of copper and copper alloy is incompatible with a non-ferrous section made of any of aluminum, aluminum alloy, titanium, titanium alloy, nickel and nickel alloy;
- a non-ferrous end-tab made of either of titanium and titanium alloy is incompatible with a non-ferrous section made of any of aluminum, aluminum alloy, copper, copper alloy, nickel and nickel alloy;
- a non-ferrous end-tab made of either of nickel and nickel alloy is incompatible with a non-ferrous section made of any of aluminum, aluminum alloy, copper, copper alloy, titanium and titanium alloy;
- a non-ferrous section made of either of aluminum and aluminum alloy is incompatible with a non-ferrous end-tab made of any of copper, copper alloy, titanium, titanium alloy, nickel and nickel alloy;
- a non-ferrous section made of either of copper and copper alloy is incompatible with a non-ferrous end-tab made of any of aluminum, aluminum alloy, titanium, titanium alloy, nickel and nickel alloy;
- a non-ferrous section made of either of titanium and titanium alloy is incompatible with a non-ferrous end-tab made of any of aluminum, aluminum alloy, copper, copper alloy, nickel and nickel alloy; and
- a non-ferrous section made of either of nickel and nickel alloy is incompatible with a non-ferrous end-tab made of any of aluminum, aluminum alloy, copper, copper alloy, titanium and titanium alloy.

* * * * *